United States Patent [19]
Hauck et al.

[11] 3,982,021
[45] Sept. 21, 1976

[54] COMPOSITIONS FOR THE TREATMENT OF CORONARY DISEASES CONTAINING TETRAHYDRONAPHTHYLOXY-AMINOPROPANOLS

[75] Inventors: Frederic P. Hauck, Somerville; Christopher M. Cimarusti, Hamilton; Venkatachala L. Narayanan, Hightstown, all of N.J.

[73] Assignee: E. R. Squibb & Sons, Inc., Princeton, N.J.

[22] Filed: Oct. 9, 1975

[21] Appl. No.: 621,176

Related U.S. Application Data

[60] Division of Ser. No. 203,865, Dec. 1, 1971, Pat. No. 3,935,267, which is a continuation-in-part of Ser. No. 48,458, June 22, 1970, abandoned.

[52] U.S. Cl. ............................................. 424/330
[51] Int. Cl.² ...................................... A61K 31/135
[58] Field of Search ................................... 424/330

[56] References Cited
FOREIGN PATENTS OR APPLICATIONS
1,136,918   12/1968   United Kingdom................ 424/330

*Primary Examiner*—Frederick E. Waddell
*Attorney, Agent, or Firm*—Lawrence S. Levinson; Merle J. Smith; Donald J. Barrack

[57] ABSTRACT

This invention relates to pharmaceutical compositions for the treatment of coronary diseases comprising a compound having the formula

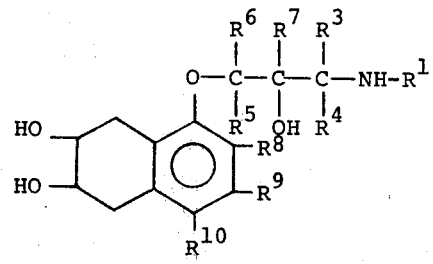

wherein $R^1$ is lower alkyl, $R^3$, $R^4$, $R^5$, $R^6$ and $R^7$ are the same or different and are hydrogen or lower alkyl, and $R^8$, $R^9$ and $R^{10}$ are the same or different and are hydrogen, lower alkyl, lower alkoxy or cycloalkyl; and a pharmaceutically acceptable carrier therefor.

4 Claims, No Drawings

COMPOSITIONS FOR THE TREATMENT OF CORONARY DISEASES CONTAINING TETRAHYDRONAPHTHYLOXY-AMINO-PROPANOLS

This application is a division of U.S. Pat. application Ser. No. 203,865, filed Dec. 1, 1971, now U.S. Pat. 3,935,267 issued Jan. 27, 1976, which is a continuation-in-part of U.S. Pat. application Ser. No. 48,458, filed June 22, 1970, and now abandoned.

This invention relates to new chemical compounds of the formula

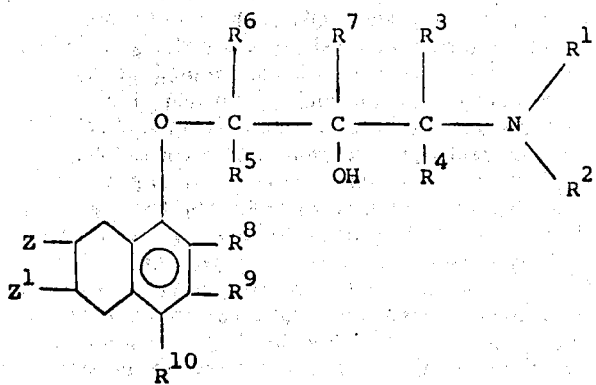

and salts of such compounds, wherein one or both of Z and $Z^1$ is hydroxy and/or $OR''$ and the other (where necessary) can be hydrogen, or Z and $Z^1$ taken together can represent O<, the radical

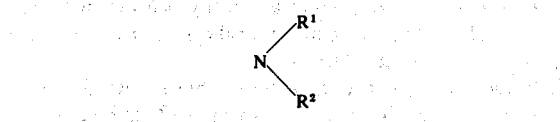

is a basic nitrogen containing radical of up to about 18 carbon atoms, $R''$ represents an acyl group, $R^3$, $R^4$, $R^5$, $R^6$ and $R^7$ are the same or different and can be hydrogen or lower alkyl, $R^8$, $R^9$ and $R^{10}$ are the same or different and can be hydrogen, lower alkyl, monocyclic aryl-lower alkyl, lower alkoxy, carboxy, and monocyclic cycloalkyl.

The term "lower alkyl" as employed herein includes both straight and branched chain radicals of up to and including eight carbon atoms, for instance, methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl and the like.

The monocyclic aryl-lower alkyl groups include benzyl, phenethyl and the like.

The term "lower alkoxy" includes straight and branched chain radicals of the structure RO- wherein R includes any of the above lower alkyl groups.

The "amino" groups include unsubstituted amino or mono- or di-lower alkyl-amino groups, wherein lower alkyl is as defined above, such as amino, methyl amino, ethyl amino, isopropyl amino, heptylamino, dimethyl amino, diethyl amino, methyl ethyl amino, methyl butyl amino, ethyl i-propyl amino and the like.

The acyl radicals represented by $R''$ include lower fatty acid radicals such as acetyl, propionyl, butyryl, isobutyryl and the like, as well as long chain fatty acid radicals such as hexanoyl, heptanoyl, decanoyl, dodecanoyl and the like, monocyclic aryl and aralkanoic acid radicals such as benzoyl, phenacetyl and the like.

The term "monocyclic aryl" as employed herein contemplates monocyclic carbocyclic aryl radicals, for instance, phenyl and substituted phenyl radicals, such as lower alkyl phenyl (e.g., o-, m- or p-tolyl, ethylphenyl, butylphenyl and the like, di(lower alkyl)phenyl (e.g., 2,4-dimethylphenyl, 3,5-diethylphenyl and the like) halophenyl (e.g., chlorophenyl, bromophenyl, iodophenyl, fluorophenyl), o-, m- or p-nitrophenyl, dinitrophenyl, (e.g., 3,5-dinitrophenyl, 2,6-dinitrophenyl and the like), and trinitrophenyl (e.g., picryl).

The expression "monocyclic cycloalkyl" includes cyclic radicals containing from 3 to 6 ring members (e.g., cyclopropyl, cyclobutyl, cyclopentyl and cyclohexyl).

In the basic nitrogen containing radical

 (II)

in formula I, $R^1$ and $R^2$ each represents hydrogen, lower alkyl, lower alkenyl, hydroxy-lower alkyl and phenyl-lower alkyl forming such basic groups as amino, lower alkylamino, e.g., methylamino, ethylamino, isopropylamino, di(lower alkyl)amino, e.g., dimethylamino, diethylamino, dipropylamino, lower alkenylamino, e.g., allylamino, di(lower alkenyl)amino, e.g., diallylamino, (hydroxy-lower alkyl)amino, e.g., hydroxyethylamino, di(hydroxy-lower alkyl)amino, e.g., di(hydroxyethyl)amino, phenyl(lower alkyl)amino, e.g., benzylamino, phenethylamino, N-(lower alkyl)phenyl(lower alkyl)amino, e.g., N-methylbenzylamino, and the like.

The

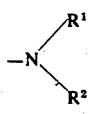

radical may form a heterocyclic radical. The symbols $R^1$ and $R^2$ may together represent the carbon (and hydrogen) and the oxygen, sulfur or nitrogen atoms which, with the nitrogen or carbon atom in the above group, form a 5- or 6-membered nitrogen heterocyclic containing not more than one hetero atom in addition to the nitrogen already shown in the group and less than 21 atoms in the radical (excluding hydrogen). The heterocyclic radicals may include one to three substituents including lower alkoxy or lower alkyl as defined hereinbefore; trifluoromethoxy; trifluoromethylmercapto; N,N-dialkylsulfamoyl groups, such as N,N-dimethylsulfamoyl; lower alkanoyl groups

where R is lower alkyl) as defined hereinbefore, such as acetyl, propionyl, and the like; hydroxy-lower alkyl, such as hydroxymethyl, 2-hydroxyethyl or the like; hydroxy-lower alkoxy-lower alkyl, such as 2-(2-hydroxy-ethoxy)ethyl, or the like; lower alkanoyl-lower alkyl, such as 2-heptanoyloxyethyl; carbon lower alkoxy, such as carbomethoxy, carboethoxy, carbopropoxy, or the like; or 2-(lower alkanoyloxy-lower alkoxy)lower alkyl such as 2-(decanoyloxyethoxy)ethyl, or the like.

Illustrative of the heterocyclic radicals represented by

are the following: piperidino; (lower alkyl)piperidino [e.g., 2-, 3-, or 4-(lower alkyl)piperidino or 4-(N-lower alkyl)piperidino, such as 2-(ethyl)piperidino or 4-(N-isopropyl)piperidino]; di(lower alkyl)piperidino [e.g., 2,4-, 2,5- or 3,5-di(lower alkyl)piperidino, such as 2,4-dimethyl piperidino or 2,5di-t-butyl piperidino]; (lower alkoxy)piperidino [e.g., 2-methoxypiperidino or 3-methoxypiperidino]; hydroxypiperidino [e.g., 3-hydroxy- or 4-hydroxypiperidino]; aminomethylpiperidino [e.g., 4-aminomethylpiperidino]; pyrrolidino; (lower alkyl)pyrrolidino [e.g., 3-methylpyrrolidino]; di(lower alkyl)pyrrolidino [e.g., 3,4-dimethylpyrrolidino]; (lower alkoxy)pyrrolidino [e.g., 2-methoxypyrrolidino]; morpholino; (lower alkyl)morpholino [e.g., 3-methylmorpholino]; di(lower alkyl)morpholino, [e.g., 3,5-dimethylmorpholino]; (lower alkoxy)morpholino, [e.g., 2-methoxymorpholino]; thiamorpholino; (lower alkyl)thiamorpholino [e.g., 3-methylthiamorpholino]; di(lower alkyl)thiamorpholino, [e.g., 3,5-dimethylthiamorpholino], (lower alkoxy)thiamorpholino, [e.g., 3-methoxythiamorpholino]; piperazino; (lower alkyl)piperazino, [e.g., $N^4$-methylpiperazino]; di(lower alkyl)piperazino, [e.g., 2,5-dimethylpiperazino or 2,6-dimethylpiperazino]; (lower alkoxy)piperazino, [e.g., 2-methoxypiperazino]; (hydroxy-lower alkyl)piperazino, [e.g., $N^4$-(2-hydroxyethyl)piperazino]; (lower alkanoyloxy-lower alkyl)piperazino, [e.g., $N^4$-(2-heptanoyloxyethyl)piperazino or $N^4$-(2-propionyloxyethyl)piperazino]; (hydroxy-lower alkoxylower alkyl)piperazino, [e.g., (hydroxymethoxymethyl)piperazino]; (carbo-lower alkoxy)piperazino, [e.g., $N^4$-(carbomethoxy-, carboethoxy-, or carbopropoxy)piperazino]; piperidyl; (lower alkyl)piperidyl [e.g., 1-, 2-, 3- or 4-(lower alkyl)piperidyl, such as 1-N-methylpiperidyl or 3-ethylpiperidyl]; di(lower alkyl)piperidyl, [e.g., 2,4-, 2,5-, or 3,5-di(lower alkyl)piperidyl wherein lower alkyl is methyl, ethyl, n-propyl, isopropyl, etc.];

lower alkoxy piperidyl, [e.g., 3-methoxypiperidyl or 2-ethoxypiperidyl]; hydroxypiperidyl [e.g., 3-hydroxy- or 4-hydroxypiperidyl]; aminomethylpiperidyl, [e.g., 4-aminoethylpiperidyl]; pyrrolidyl; lower alkyl pyrrolidyl, [e.g., 1-N-methylpyrrolidyl]; di(lower alkyl)pyrrolidyl, [e.g., 2,3-dimethylpyrrolidyl]; lower alkoxy pyrrolidyl, [e.g., 4-N-methoxypyrrolidyl]; morpholinyl; (lower alkyl)morpholinyl, [e.g., 3-methylmorpholinyl]; di(lower alkyl)morpholinyl, [e.g., 3-methyl-4-N-ethylmorpholinyl]; (lower alkoxy)morpholinyl, e.g., 2-ethoxymorpholinyl]; thiamorpholinyl; (lower alkyl)thiamorpholino, [e.g., 3-ethylthiamorpholinyl]; di(lower alkyl)thiamorpholinyl, [e.g., 3-methyl-4-N-ethylthiamorpholinyl]; lower alkoxy thiamorpholino, [e.g., 3-methoxythiamorpholinyl]; piperazinyl; alkyl, dialkyl, alkoxy or hydroxy-lower alkyl substituted piperazinyl.

The compounds of formula I form acid addition salts with inorganic and organic acids. These acid addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic or organic acid. Illustrative are the hydrohalides, especially the hydrochloride and hydrobromide which are preferred, sulfate, nitrate, phosphate, borate, acetate, oxalate, tartrate, maleate, citrate, succinate, benzoate, ascorbate, salicylate, methanesulfonate, benzenesulfonate, toluenesulfonate and the like. Quaternary ammonium salts are also formed, e.g., by reacting the free base with an alkylating agent, e.g., lower alkyl halide such as methyl chloride, ethyl bromide or the like, lower alkyl sulfate such as methyl sulfate, aralkyl halides such as benzyl chloride, aralkyl sulfates such as benzyl sulfate and the like.

Preferred are those compounds wherein $R^3$, $R^4$, $R^5$, $R^6$, $R^7$, $R^8$, $R^9$ and $R^{10}$ are all hydrogen, $R^1$ is hydrogen or lower alkyl, especially hydrogen and $R^2$ is lower alkyl, especially isopropyl. The compounds of this invention are useful as antifibrillatory agents, for example, in arresting cardiac arrhythmia in mammals, e.g., by inhibition of beta adrenergic receptors in the myocardium. For this purpose a compound of formula I or a physiologically acceptable acid addition salt may be incorporated in a conventional dosage form such as tablet, capsule, elixir, injectable or the like along with the necessary carrier material, excipient, lubricant, buffer or the like. Single or divided doses of about 5 to 25 mg/kg, preferably about 4 to 10 mg/kg, two to four times daily may be administered in dosage forms as described above.

Examples of compounds falling within the present invention include, but are not limited to, the following:

1. 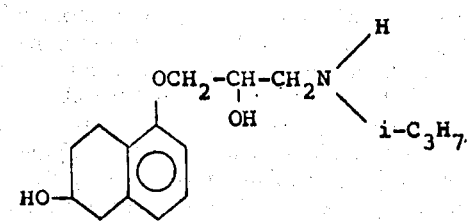

2. 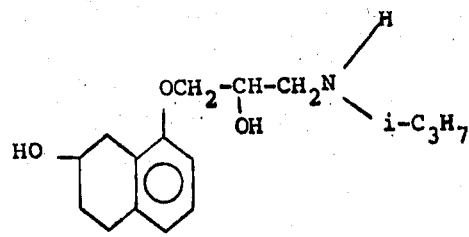
3. 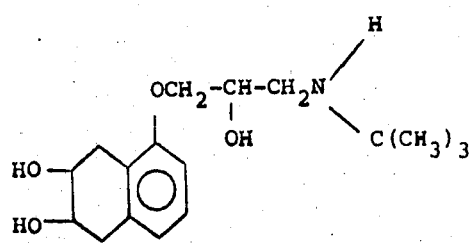
4. 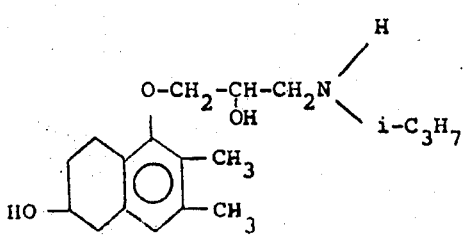
5. 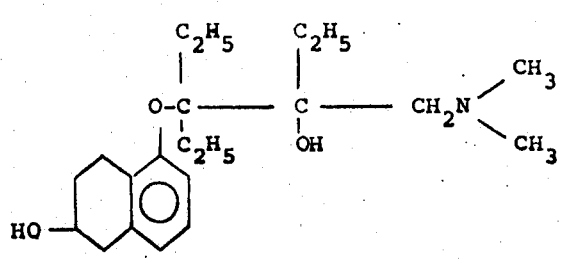
6. 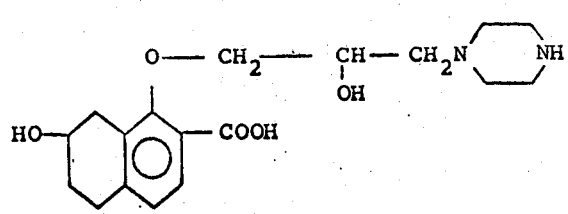
7. 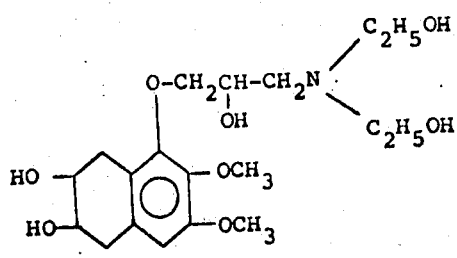

8. 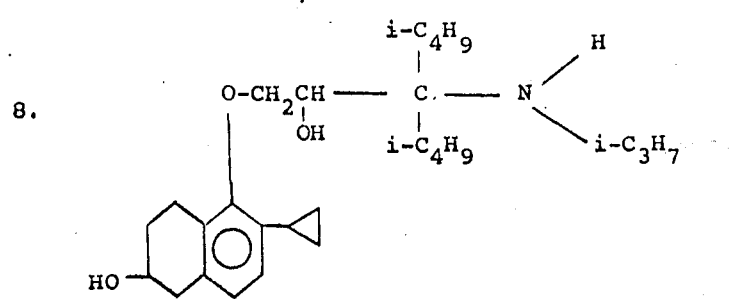
9. 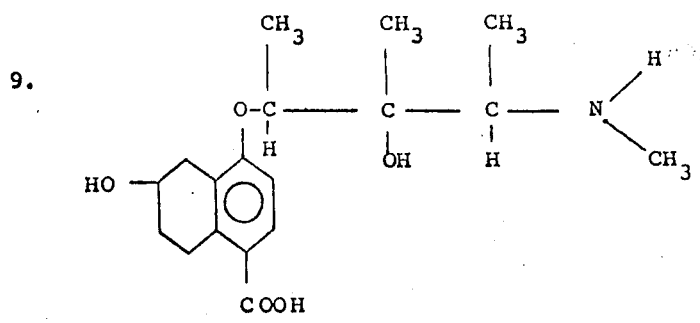
10. 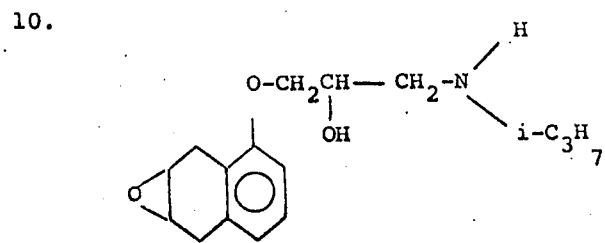
11. 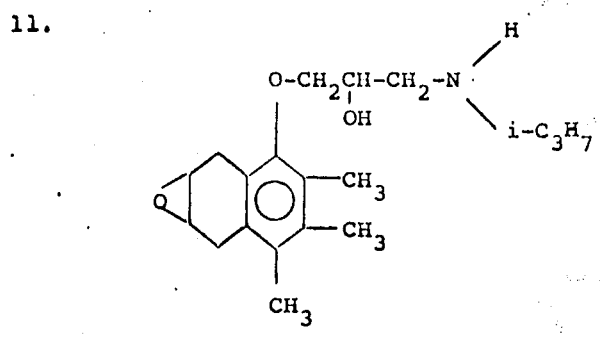
12. 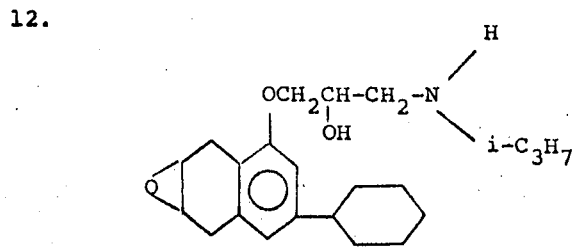

13.
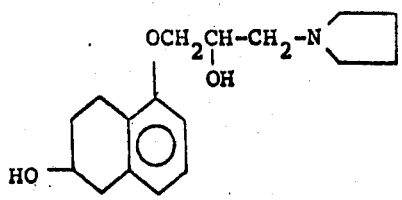
14.
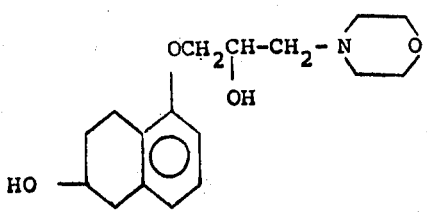
15.
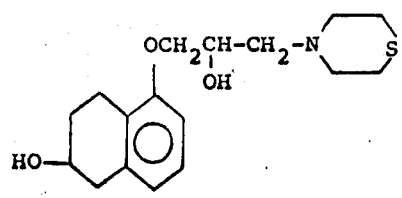
16.
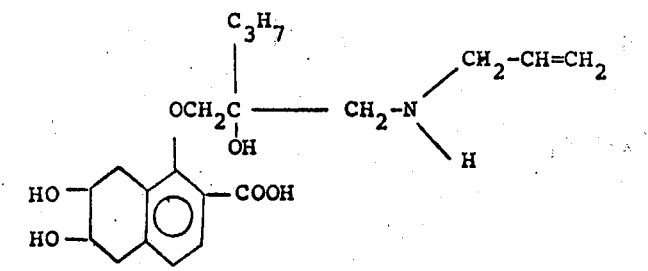
17.
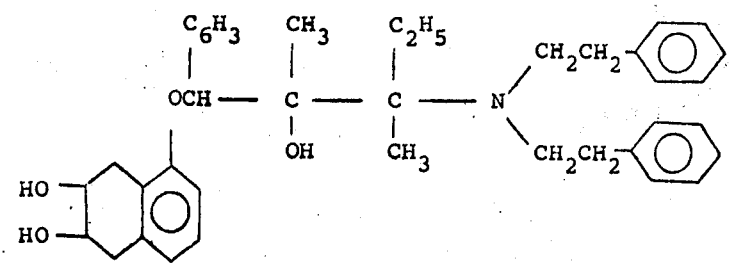

18. 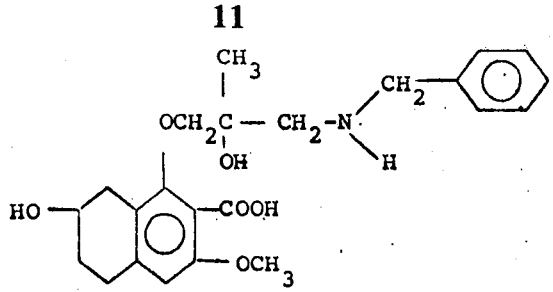
19. 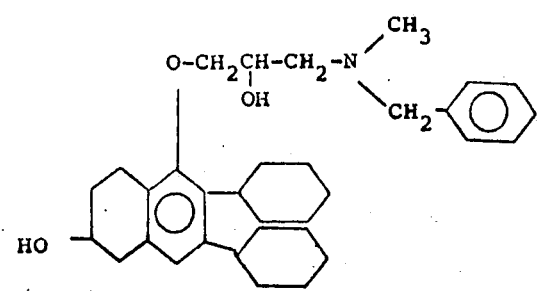
20. 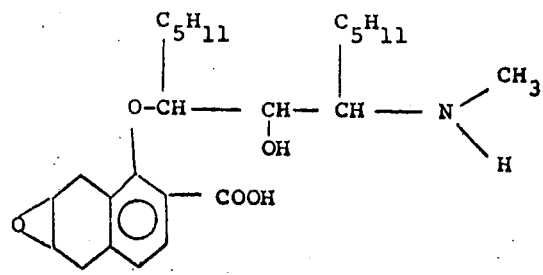
21. 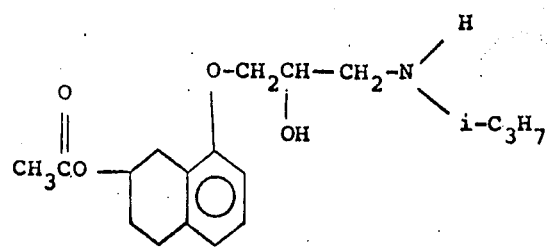
22. 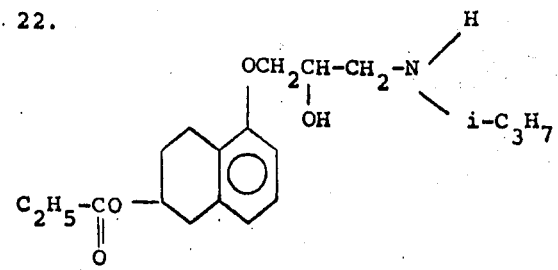

23.

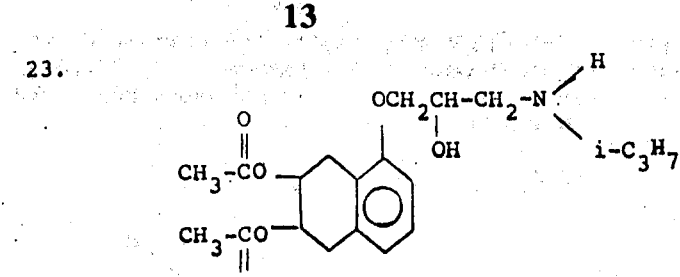

24.

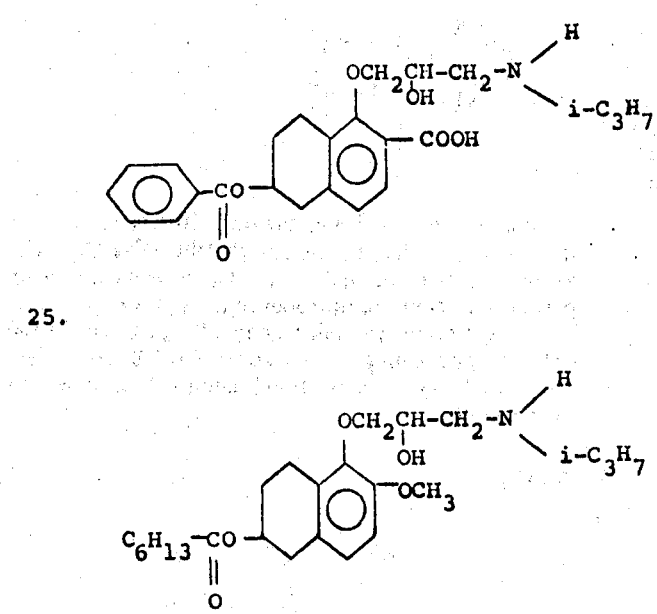

25.

The compounds of formula I can be prepared by several methods.

In a first method for preparing compounds of formula I wherein one of Z and $Z^1$ is hydroxy and the other is hydrogen, a 1-(5,8-dihydronaphthyloxy)-3-(substituted-amino)-2-propanol prepared as described in copending application Ser. No. 768,176, filed Oct. 16, 1968, issued Oct. 13, 1970 as U.S. Pat. No. 3,534,085 and having the structure wherein $R^1$ through $R^{10}$ are as defined hereinbefore, is reacted with diborane or a mono- or dilower alkyl borane followed by an oxidative workup to give a mixture of alcohols of formula I wherein one Z and $Z^1$ is hydroxyl and the other hydrogen. The mixture can then be separated by column chromatography or fractional recrystallization of suitable derivatives such as the hydrochloride salt.

In another method for preparing compounds of for- (II)

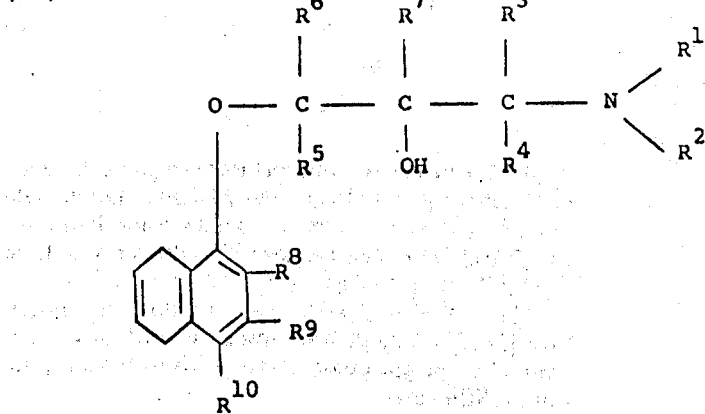

mula I wherein Z and $Z^1$ taken together are O<, or one of Z and $Z^1$ is hydroxy and the other hydrogen, a naphthol of the structure (III)

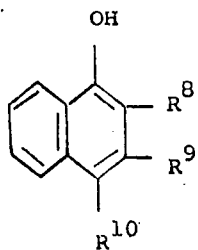

is reduced with a metal like sodium or lithium in liquid ammonia containing an alkanol such as ethanol, isopropanol, t-butanol or the like [e.g., by the procedure described in Organic Synthesis, Coll. Vol. 4, page 887 (1963)] to obtain the 5,8-dihydronaphthol of the formula (IV)

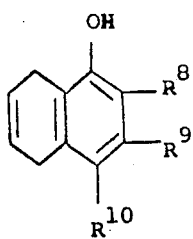

The compound of formula IV is made to react with an epoxide of the formula (V)

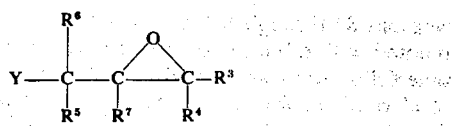

(Y is chlorine or bromine), to obtain a 1-(2,3-epoxy propoxy)-5,8-dihydronaphthalene of the formula (VI)

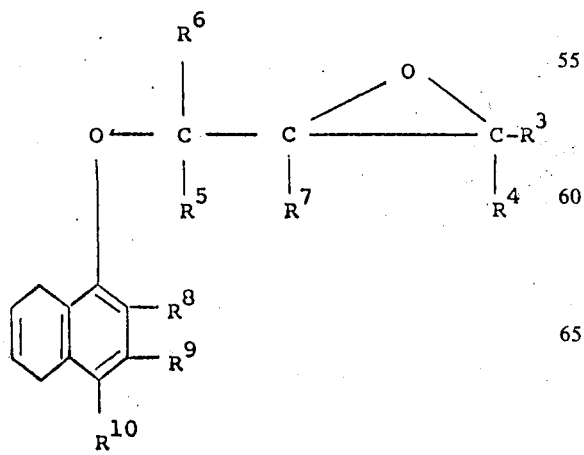

The 1-(2,3-epoxy propoxy)-5,8-dihydronaphthalene is then converted to the corresponding 1-[2,3-(epoxy)-propoxy]-6,7-epoxy-5,6,7,8-tetrahydronaphthalene of the structure (VII)

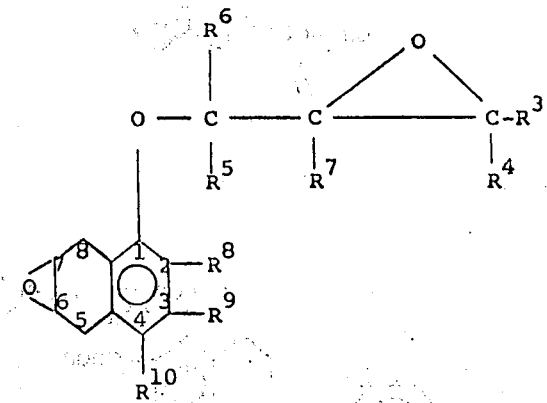

by reacting the dihydronaphthalene (formula VI) in an inert solvent such as methylene chloride ($CH_2Cl_2$), with an organic peracid such as m-chloroperbenzoic acid, perbenzoic acid, pernitrobenzoic acid or peracetic acid. The tetrahydronaphthalene VII can be converted to the corresponding 1-[(6,7-epoxy-5,6,7,8-tetrahydro-1-naphthyl)oxy]-3-(substituted amino)-2-propanol of the structure (VIII)

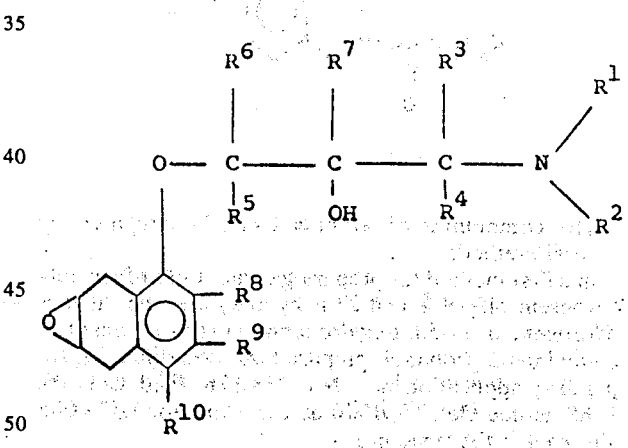

by refluxing the tetrahydronaphthalene (formula VII) with an amine of the formula

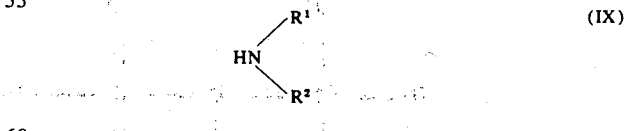

(IX)

in an inert organic solvent, such as n-propanol, benzene or toluene, e.g., for about 16 to 24 hours. An alternate procedure involves heating the reactants in a Parr pressure reactor at a temperature within the range of from about 70° to about 110° for 6 – 12 hours.

The 1-[6,7-epoxy-5,6,7,8-tetrahydro-1-naphthyl)-oxy]3-(substituted amino)-2-propanol VIII can be converted to the corresponding 6 or 7-hydroxy compound of the structure (X)
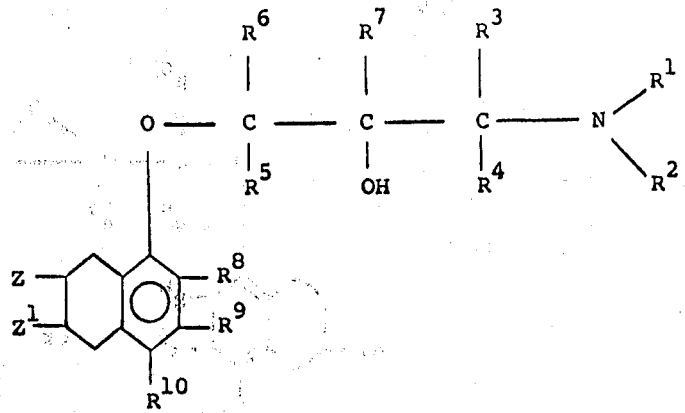

wherein Z or $Z^1$ is hydroxy and the other is hydrogen by reduction with a complex metal hydride such as lithium aluminum hydride or sodium borohydride or catalytically over a noble metal catalyst such as platinum oxide, followed by separation for example by chromatography.

1,2,3,4-Tetrahydro-5-[2-hydroxy-3-(substituted amino)-propoxy]-2(or3)-naphthols of the structure X wherein one of Z and $Z^1$ is hydroxy and the other is hydrogen can be prepared employing a 6 or 7-methoxy-1-tetralone as the starting material, i.e.,

XI

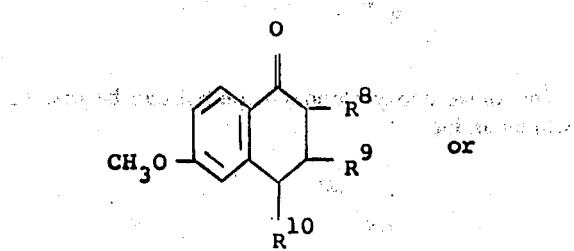

XII

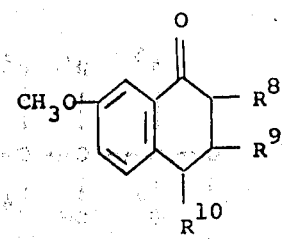

by reacting the 6 or 7-methoxy-1-tetralone with a dehydrogenating agent such as sulfur or palladium on charcoal at a temperature within the range of from about 240° to about 280°C. and preferably from about 245° to about 265°C., and then separating out, e.g., by chromatography, 6 or 7-methoxy-1-naphthol of the structure

XIII

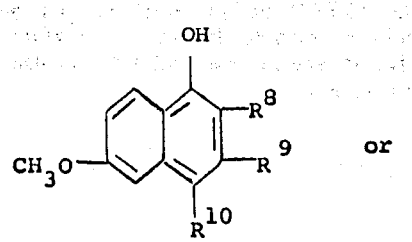 or

XIV

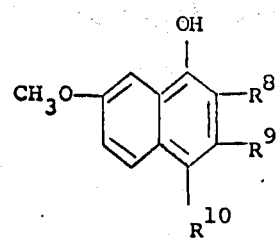

The methoxy naphthol is then subjected to a Birch reduction wherein it is reacted with lithium in the presence of liquid ammonia to form 5-hydroxy-3,4-dihydro-2(or 3) (1H)-naphthalenone after acidic hydrolysis.

XV

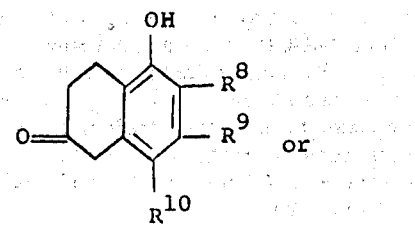 or

XVI

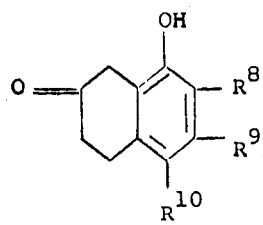

The naphthalenone is reacted with a reducing agent, such as an alkali metal borohydride, for example, sodium borohydride, in an alcohol solvent, boiling below about 100°C., such as methanol, at a temperature below about 100°C., and preferably below about 30°C.; acetic acid is added to the reaction mixture and the solvent is removed to give 5,6,7,8-tetrahydro-1, 6 (or 7)-naphthalenediol

XVII

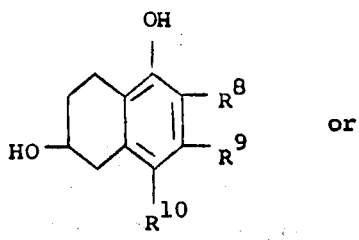 or

XVIII

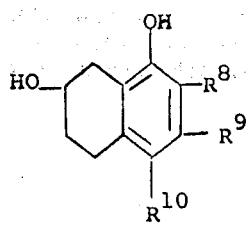

The tetrahydronaphthalenediol is then converted to an alkali metal salt by mixing with an alkali metal alkoxide such as NaOCH$_3$ in an alcohol solvent boiling below about 100°, such as methanol, and removing the solvent in vacuo to give the dry salt which is reacted with an epoxide of formula V, such as epichlorohydrin in a solvent such as dimethylsulfoxide (as described herein) to form 1,2,3,4-tetrahydro-5-[2,3-epoxy propoxy]-2 (or 3)-naphthol

XIX

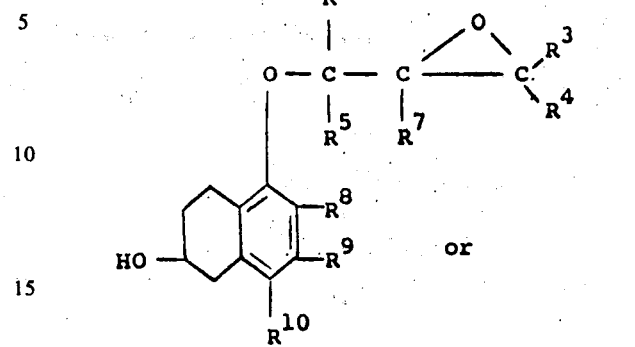

XX

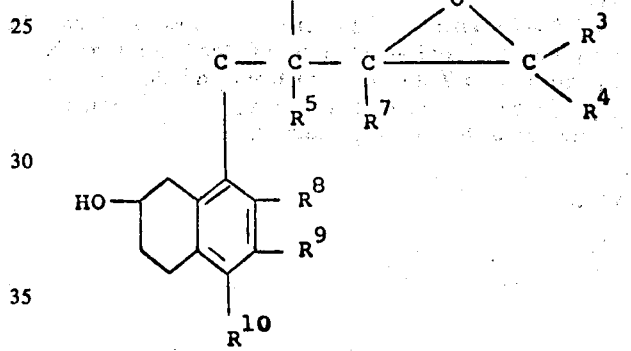

The above epoxy-propoxy-naphthol can be reacted with an amine

     (IX)

as described hereinbefore to form compounds of the invention of the structure

XXI

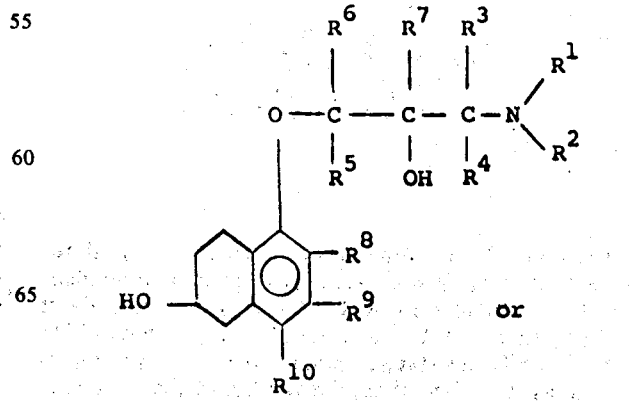

XXII

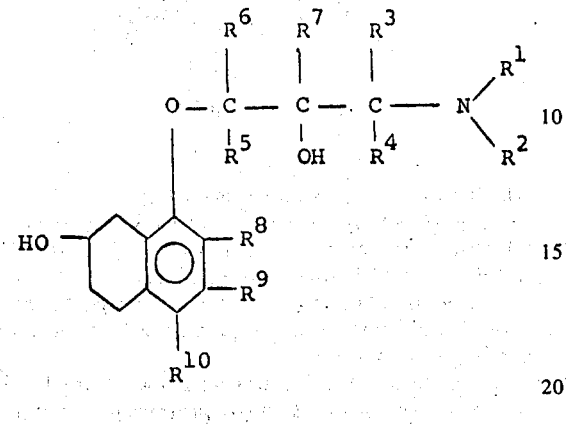

2,3-trans (or cis)-1,2,3,4-tetrahydro-5-[2-hydroxy-3-(substituted amino)propoxy]-2,3-naphthalenediols of the structure

XXIII

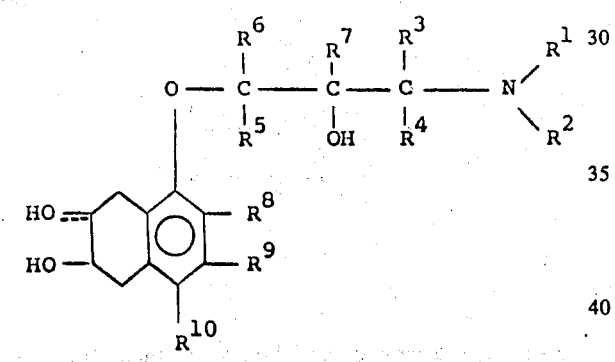

can be prepared by forming a 5,8-dihydronaphthol of the structure

III

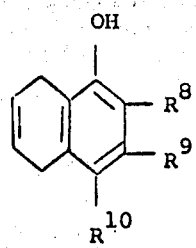

as described hereinbefore and dissolving the 5,8-dihydronaphthol in acetic anhydride and an organic base such as pyridine to form the corresponding acetate of the structure

XXIV

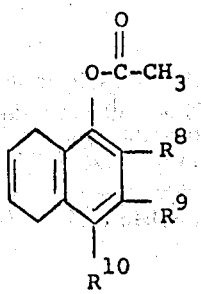

The 2,3-trans isomer is prepared from the acetate by dissolving the acetate in acetic acid, and then treating the solution with from about 2 to about 4 equivalents of silver acetate and from about 1 to about 2 equivalents of iodine. The mixture is then heated at a temperature of from about 80° to about 120°C for a period of from about 1 to about 24 hours, under nitrogen, to thereby form trans-5,6,7,8-tetrahydro-1,6,7-naphthalenetriol of the structure XXV after basic hydrolysis:

XXV

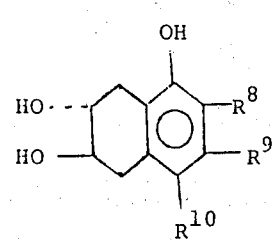

The trans-5,6,7,8-tetrahydro-1,6,7-naphthalenetriol can be converted to the 2,3-trans-1,2,3,4-tetrahydro-5-[2,3-(epoxy)-propoxy]-2,3-naphthalenediol of the structure

XXVI

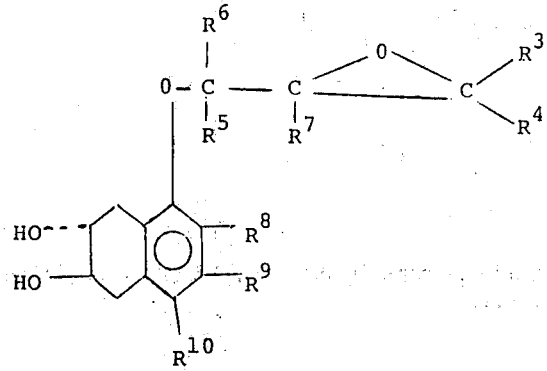

by reacting the naphthalenetriol XXV with an alkali metal alkoxide, such as sodium methoxide in an alcohol solvent boiling below about 100°C, such as methanol under nitrogen and then, after removal of solvent, stirring the residue in a dipolar aprotic solvent such as dimethylsulfoxide, hexamethylphosphoramide or dimethylformamide, and an epoxide of the structure V, such as epichlorohydrin, under nitrogen.

The 2,3-trans-1,2,3,4-tetrahydro-5-[2,3(epoxy)-propoxy]2,3-naphthalenediol is then reacted with a substituted amine of the structure

to form 2,3-trans-1,2,3,4-tetrahydro-5-[2-hydroxy-3-(substituted amino)propoxy]-2,3-naphthalenediol of the structure

XXVII

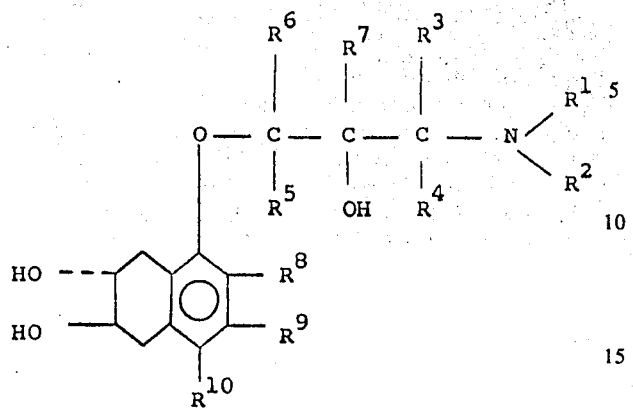

The corresponding cis isomer of the structure

XXVIII

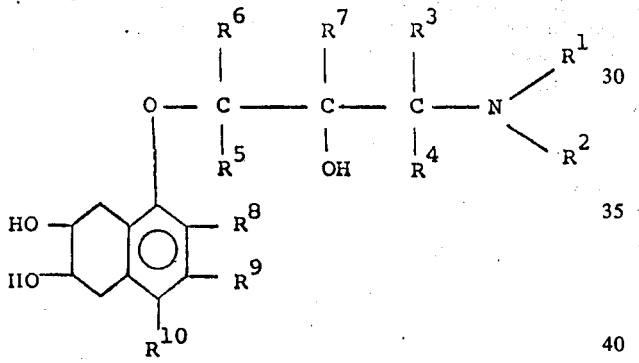

can be prepared by dissolving the dihydronaphthalene acetate

XXIV

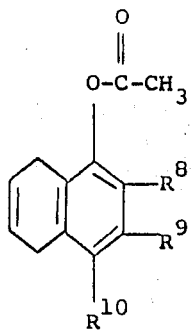

in acetic acid and water (from 92 to 98 % acetic acid, preferably 96% acetic acid), and then treating the solution with silver acetate and iodine and heating under nitrogen, as described in the preparation of the trans-isomer, to form the cis-5,6,7,8-tetrahydro-1,6,7-naphthalenetriol after basic hydrolysis

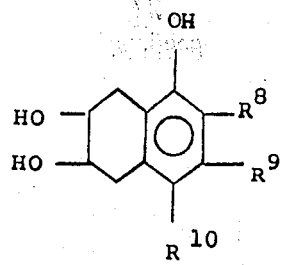

which can be converted to the 2,3-cis-1,2,3,4-tetrahydro-5-[2,3-(epoxy)-propoxy]-2,3-naphthalenediol, which in turn can be converted to the 2,3-cis-1,2,3,4-tetrahydro-5-[2-hydroxy-3-(substituted amino)propoxy]-2,3-naphthalenediol in a manner similar to that described with respect to the preparation of the correpsonding trans isomer.

Alternatively, the 2,3-trans-1,2,3,4-tetrahydro-5-[2-hydroxy-3-(substituted-amino)propoxy]-2,3-naphthalenediol isomer XXVII can be prepared from a 5,8-dihydro-1-naphthol of the structure

III

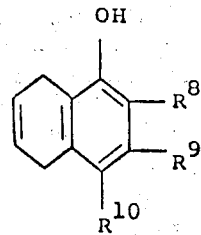

prepared as described hereinbefore, by mixing a cooled solution (temperature less than about 30°C.) of 5,8-dihydro-1-naphthol in ethyl acetate with m-chloroperbenzoic acid and mixing the resulting slurry with a mixture of ethyl ether and aqueous sodium bicarbonate, to form 5,6,7,8-tetrahydro-6,7-epoxy-1-naphthol

XXX

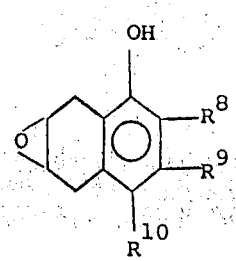

and reacting the 5,6,7,8-tetrahydro-6,7-epoxy-1-naphthol in tetrahydrofuran with aqueous perchloric acid at a temperature within the range of from about 0° to about 60°C., to form trans-5,6,7,8-tetrahydro-1,6,7-naphthalenetriol XXV which can be converted to the 2,3-trans-1,2,3,4-tetrahydro-5-[2,3-(epoxy)propoxy]-

2,3-naphthalenediol XXVI which in turn can be converted to the 2,3-trans-1,2,3,4-tetrahydro-5-[2-hydroxy-3-(substituted amino)propoxy]-2,3-naphthalenediol XXVII in a manner similar to that described hereinbefore.

A mixture of 1,2,3,4-tetrahydro-5-[2-hydroxy-3-(substituted amino)-propoxy]-2-naphthol and the corresponding 3-naphthol (formulae XXI and XXII) can be prepared from 5,6,7,8-tetrahydro-6,7-epoxy-1-naphthol (formula XXX) as follows:

The tetrahydro compound XXX is reduced to mixture of the 2-naphthol XXI and the 3-naphthol XXII by reduction with a complex metal hydride such as lithium aluminum hydride or catalytically by hydrogen in the presence of a noble metal catalyst as described hereinbefore, followed by conversion to the corresponding epoxides and then amino alcohols in a manner similar to that described hereinbefore.

Esters of the compounds of formula I, i.e.,

XXXI

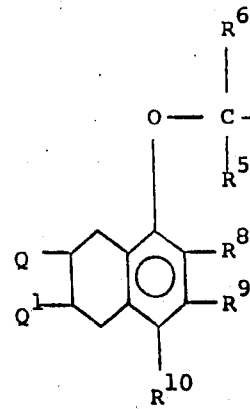

wherein one of Q and Q$^1$ is

wherein R$^{12}$ is lower alkyl, or monocyclic aryl or lower alkyl-monocyclic aryl, and the other is hydrogen, can be prepared by reacting a compound of formula I wherein one of Z and Z$^1$ is hydroxy and the other hydrogen, with acetone or an aldehyde of the structure $$R^{12}-\overset{H}{\underset{}{C}}=O \quad (XXXII)$$

wherein R$^{12}$ is lower alkyl, monocyclic aryl or lower alkyl-monocyclic aryl in the presence of a solvent boiling below about 100°C., such as benzene of chloroform to form an oxazolidine compound of the structure

XXXIII

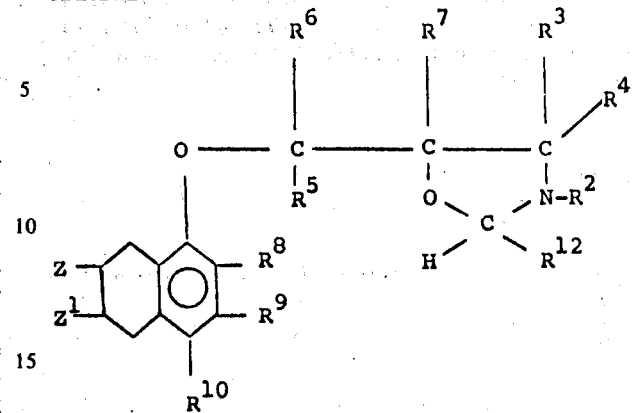

and then reacting the oxazolidine with an acid anhydride or an acid halide exemplified by the acids mentioned hereinbefore, in the presence of a suitable base such as pyridine to give the ester of the oxazolidine of the structure

XXXIV

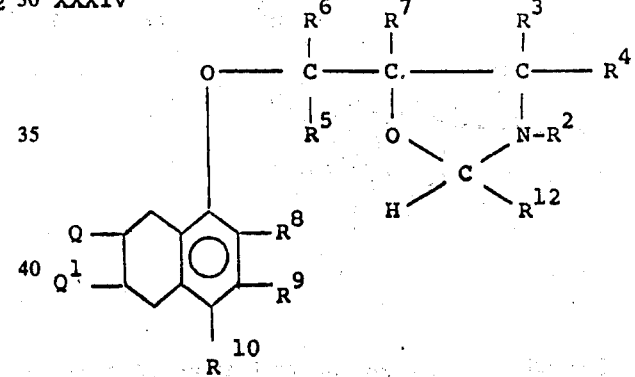

Alternatively, the reaction product of the oxazolidine and the acid anhydride or halide can be reacted with phosgene to form a compound of the structure XXXIVa

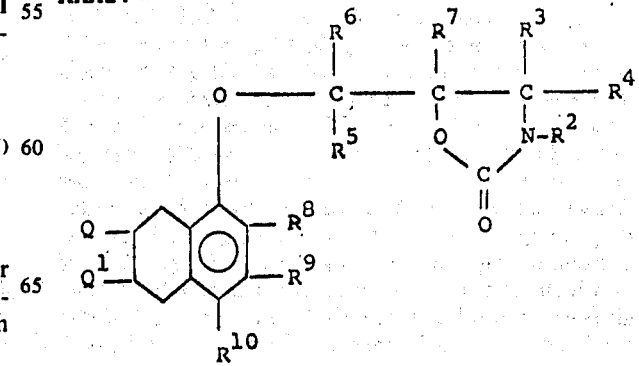

The oxazolidine compounds of XXXIV or XXXIVa can be converted to an acid addition salt of formula I by acidic hydrolysis employing dilute aqueous acid as described hereinbefore, i.e.,

XXXV

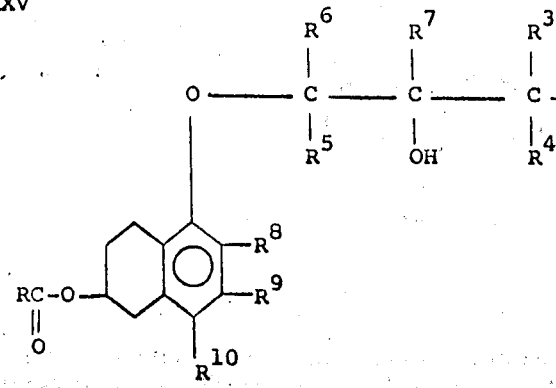

or

XXXVI

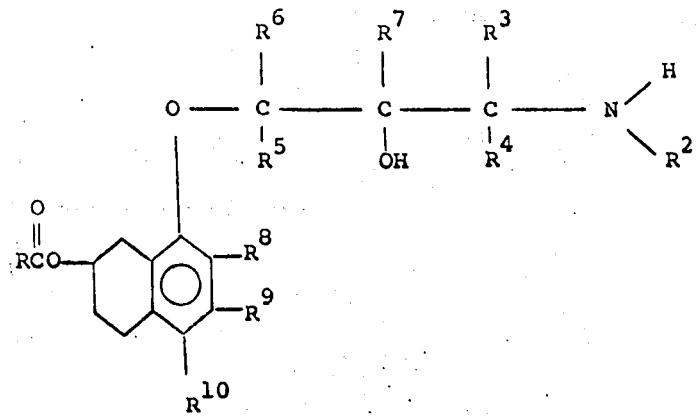

Anal. Calc'd. for $C_{13}H_{14}O_3$: C, 71.54; H, 6.47. Found: C, 71.50; H, 6.77.

b. 1-[(6,7-Epoxy-5,6,7,8-tetrahydro-1-naphthyl)oxy]-3-(isopropylamino)-2-propanol A solution of 4.3 g. (0.02 m.) of 2,3-epoxypropyl 6,7-epoxy-5,6,7,8-tetrahydro-1-naphthyl ether in 34 ml. (0.4 m.) of isopropyl amine is placed in a small Parr bomb and heated in an oil bath to approximately 70° to 80° (pressure gauge registered 50) for 10 hours. Evaporation of excess isopropyl amine in vacuo yields 5.3 g. of a brown sticky solid. Crystallization from ether-pentane gives 2 g. of off-white solid; m.p. 106°–110°. A second recrystallization from ether gives 0.6 g. of white solid as the first crop, m.p. 115°–117° C., $\lambda_{Nujol}^{max}$, 3320 $cm^{-1}$ (NH), 1330–1350 $cm^{-1}$ (epoxy), TCDCl$_3$ 8.8 – 9.0 [—CH(CH$_3$)$_2$].

Calc'd. for $C_{16}H_{23}NO_3$: C, 69.28; H, 8.36; N, 5.05. Found: C, 69.47; H, 8.33; N, 5.09.

EXAMPLE 2

1,2,3,4-Tetrahydro-5-[2-hydroxy-3-(isopropylamino)-propoxy]-2-naphthol and/or
1,2,3,4-tetrahydro-5-[2-hydroxy-3-(isopropylamino)-3-naphthol To a well-stirred slurry of 10 g. of lithium aluminum hydride in 250 ml. of ethyl ether is added dropwise a solution of 5.5. g. (0.02 m.) of 2,3-epoxy-1,2,3,4-tetrahydro-5-[2-hydroxy-3-(isopropylamino)propoxy]-naphthalene in 100 ml. of dioxane. After heating under The following Examples further illustrate the invention:

EXAMPLE 1

1-[(6,7-Epoxy-5,6,7,8-tetrahydro-1-naphthyl)oxy]-3-(isopropylamino)-2-propanol a. 2,3-Epoxypropyl 6,7-epoxy-5,6,7,8-tetrahydro-1-naphthyl ether To a well-stirred solution of 7 g. (0.03 m.) of 1-(2,3-epoxy-propoxy)-5,8-dihydro-naphthalene (prepared as described in application Ser. No. 768,176, filed Oct. 16, 1968, issued Oct. 13, 1970, as U.S. Pat. No. 3,534,085) in 60 ml. of $CH_2Cl_2$, 7.1 g. (0.03 m.) of 85% m-chloroperbenzoic acid in 100 ml. $CH_2Cl_2$ is added dropwise at such a rate that the temperature is maintained between 25° to 30°C. The mixture is stirred overnight at room temperature. The resulting precipitate (m-chlorobenzoic acid) is filtered off and the $CH_2Cl_2$ extract is washed successively with sat. NaHCO$_3$ solution, and water. After drying (MgSO$_4$), the solution is evaporated in vacuo to give 7.2 g. (95%) of oil which solidifies. A sample recrystallized from ether gives white needles, m.p. 85°–87°; $\lambda_{Nujol}^{max}$ 1330–1350 $cm^{-2}$ (epoxy), $\tau$CDCl$_3$ absence of vinyl protons 4.0–4.2 region.

reflux for 12 hours, the mixture is freed of excess hydride by the addition of aqueous potassium carbonate solution and filtered. Removal of solvent leaves a mixture of alcohols which is taken up in benzene and chromatographed on 150 g. of basic alumina of Activity grade III. Elution with mixtures of chloroform-methanol elutes the desired products. Seeding with crystalline material (Example 3) induces crystallization of the 2-isomer, and the 3-isomer (Example 7).

EXAMPLE 3

1,2,3,4-Tetrahydro-5-[2-hydroxy-3-(isopropylamino)-propoxy]-2-naphthol, oxalate salt (1:1)

a. 6-Methoxy-1-naphthol

An intimate mixture of 81.5 g. (0.462 mole) of 6-methoxy-1-tetralone and 14.5 g. (0.465 mole) of sulfur is heated at 240°–250° for 6 hours and distilled to give 39.8 g. of oil, b.p. 158°–164° (0.3 – 0.5 mm.). Chromatography over Activity IV alumina followed by recrystallization from 9:1 hexane-ethyl acetate gives 23.9 g. (29%) of 6-methoxy-1-naphthol in 3 crops. m.p. 84°–86° (lit m.p. 84.5°–85°) Tet., 19 (12) 1919 (1963).

b. 5-Hydroxy-3,4-dihydro-2(1H)-naphthalenone

To a stirred slurry of 8.0 g. (0.048 mole) of 6-methoxy-1-naphthol and 200 ml. of liquid ammonia held below the reflux temperature by external cooling there is added 1.05 g. (0.15 g. - atom) of lithium ribbon over 25 minutes. After a further 10 minutes at this temperature, 20 ml. of ethanol is added over 30 minutes. As the blue color fades, the ammonia is evaporated and the residue stirred overnight under nitrogen with 50 ml. of water, 50 ml. of tetrahydrofuran and 35 ml. of conc. hydrochloric acid. Extraction with three 100 ml. portions of chloroform followed by drying and solvent removal gives 7.24 g. of solid. Recrystallization (4:1) hexane-ethyl acetate gives 5.04 g. (68%) of ketone, m.p. 168°–171° (lit m.p. 155°–162° dec.), JACS 80, 2887 (1958).

c. 5,6,7,8-Tetrahydro-1,6-naphthalenediol

A 3.7 g. (0.0235 mole) sample of 5-hydroxy-3,4-dihydro-2(1H)-naphthalenone in 125 ml. of methanol is added to a cooled solution of 1.0 g. (0.025 mole) of sodium borohydride in 25 ml. of methanol. After 150 minutes at 0°, 7.2 g. of acetic acid is added and the solvent removed in vacuo. Partitioning between water and methylene chloride gives 3.54 g. of crude product after further extraction, drying and solvent removal. Recrystallization from hexane-ethyl acetate gives 2.92 g., m.p. 126°–128.5°. (lit. m.p. 127°–128°) JACS, 80, 2887 (1958).

d. 1,2,3,4-Tetrahydro-5-[2,3-epoxy-propoxy]-2-naphthol

A solution of 2.46 g. (0.015 mole) of 5,6,7,8-tetrahydro-1,6-naphthalenediol and 810 mg. (0.015 mole) of sodium methoxide in 30 ml. of methanol is prepared under nitrogen and the solvent removed in vacuo. The resulting foam is stirred overnight with 20 ml. of dimethylsulfoxide and 1.40 g. (0.015 mole) of epichlorohydrin, poured into 200 ml. of water and extracted with four 125 ml. portions of ether. Drying and solvent removal gives 3.06 g. of oil which is purified by chromatography on silica gel (75 g.). Elution with hexane-chloroform mixtures gives a total of 1.56 g. (49%) of material with one spot on TLC.

e. 1,2,3,4-Tetrahydro-5-[2-hydroxy-3-(isopropylamino)-propoxy]-2-naphthol

A solution of 1.50 g. of epoxide in 15 ml. of isopropylamine is heated at 90° in a bomb for 8 hr. Solvent removal gives a solid which is recrystallized from acetonitrile three times to give 1.21 g., m.p. 136°–141°.

Anal. Calc'd for $C_{16}H_{25}NO_3$: C, 68.78; H, 9.02; N, 5.01. Found: C, 69.87; 69.61; H, 9.08; 9.17; N, 5.14; 5.09.

f. 1,2,3,4-Tetrahydro-5-[2-hydroxy-3-(isopropylamino)-propoxy]-2-naphthol, oxalate salt Conversion of 1,2,3,4-tetrahydro-5-[2-hydroxy-3-(isopropylamino)-propoxy]-2-naphthol to its oxalic acid salt is accomplished by mixing equimolar amounts of oxalic acid and amine in acetonitrile. The resulting solid is recrystallized twice from ethanol to give 1.19 g., m.p. 163°–164.5°.

Anal. Calc'd for $C_{18}H_{27}NO_7$: C, 58.52; H, 7.37; N, 3.79. Found: C, 58.20; H, 7.30; N, 3.91.

EXAMPLE 4

2,3-trans-1,2,3,4-Tetrahydro-5-[2-hydroxy-3-(isopropylamino)-propoxy]-2,3-naphthalenediol a. 5,6,7,8-Tetrahydro-6,7-epoxy-1-naphthol An amount of 25.0 g. (ca., 0.12 moles) of m-chloroperbenzoic acid is added over 10 min. to an ice-cooled solution of 14.6 g. (0.10 mole) of 5,8-dihydro-1-naphthol (prepared as described in Org. Syn., Coll. Vol. IV, pg. 887) in 225 ml. of ethyl acetate. After 16 hr. at ambient temperature the slurry is poured into a cooled, stirred mixture of 300 ml. each of ether and 10% sodium bicarbonate. After 15 min. the organic phase is separated, washed with water, saturated salt solution and dried. Solvent removal gives an oil which is triturated with two 100 ml. portions of boiling hexane. The residue is recrystallized from 150 ml. of 1:1 hexane-ethyl acetate to give 6.6 g. (41%) of 5,6,7,8-tetrahydro-6,7-epoxy-1-naphthol, m.p. 143°–146°. Two further recrystallizations of a small sample give the analytical sample m.p. 149.5°–151°.

Anal. Calc'd for $C_{10}H_{10}O_2$: C, 74.05; H, 6.22. Found: C, 74.01; H, 6.21 b. trans-5,6,7,8-Tetrahydro-1,6,7-naphthalenetriol

A solution of 8.0 g. (0.048 mole) of 5,6,7,8-tetrahydro-6,7-epoxy-1-naphthol in 100 ml. of tetrahydrofuran is cooled to 0° and 20 ml. of water and 0.5 ml. of 70% perchloric acid are added. After 4 hr., a further 1.5 ml. of acid is added and the solution stirred for 16 hr. at ambient temperature and diluted with 100 ml. each of ether, 10% sodium bicarbonate and saturated salt solution. The aqueous layer is separated and washed with 150 ml. of 1:1 ether-tetrahydrofuran. The organic phase is washed with saturated salt solution, dried and evaporated to give an oil which solidifies on trituration with chloroform. Recrystallization gives in two crops, 4.85 g. of solid which is recrystallized from ethyl acetate to give 3.84 g. m.p. 179.5°–181.5°. Two further recrystallizations of a small sample give the analytical specimen, m.p. 183°–184°.

Anal. Calc'd for $C_{10}H_{12}O_3$: C, 66.65; H, 6.71. Found: C, 67.05; H, 6.90.

c. 2,3-trans-1,2,3,4-Tetrahydro-5-[2,3-(epoxy)-propoxy]-2,3-naphthalenediol

A solution of 3.60 g. (0.02 mole) of 5,6,7,8-tetrahydro-1,6,7-naphthalenetriol in 100ml. of methanol is cooled to 0° and 1.08 g. (0.02 mole) of sodium methoxide in methanol added. The solvent is removed in vacuo and the residue heated at 50° at 0.05 mm. for 1 hr., dissolved in 80 ml. of dimethylsulfoxide and stirred overnight under nitrogen with 3.68 g. (0.04 mole) of epichlorohydrin. After 17 hr. the solvent is removed in vacuo, the residue dissolved in 250 ml. of water and extracted 3 times with 150 ml. of ether and 2 times with 150 ml. of chloroform. Both organic extracts are washed with excess 5% sodium hydroxide, saturated salt solution and dried. Solvent removal gives a total of 3.25 g. of solid which is recrystallized from benzene to give 2.59 g., m.p. 113°–116°.

d. 2,3-trans-1,2,3,4-Tetrahydro-5-[2-hydroxy-3-(isopropylamino)-propoxy]-2,3-naphthalenediol A solution of 2.5 g. (0.0106 mole) of 2,3-trans-1,2,3,4-tetrahydro-5-[2,3-(epoxypropoxy]-2,3-naphthalenediol in 15 ml. of isopropyl amine is heated at 80° ± 5° for 16 hr. in a Par bomb (pressure = 40 lb/in$^2$). The solution is evaporated in vacuo to give a foam which crystallizes on trituration with ether. Filtration gives 2.96 g. which is recrystallized three times from benzene to give 2.06 g., m.p. 112°–127°.

Anal. Calc'd for $C_{16}H_{25}NO_4$: C, 65.06; H, 8.53; N, 4.74. Found: C, 65.35; H, 8.44; N, 4.61.

EXAMPLE 5

2,3-cis-1,2,3,4-Tetrahydro-5-[2-hydroxy-3-(isopropylamino)-propoxy]-2,3-naphthalenediol a. cis-5,6,7,8-Tetrahydro-1,6,7-naphthalenetriol A solution of 29.2 g. (0.2 mole) of 5,8-dihydro-1-naphthol and 40 ml. of acetic anhydride in 100 ml. of pyridine is prepared. After 16 hr. the solvent is removed in vacuo and the residue dissolved in ether and washed with 200 ml. of 5% hydrochloric acid, water, 200 ml. of 10% sodium hydroxide, saturated salt solution and dried. Solvent removal gives 34.2 g. (90.5%) of crude acetate which is dissolved in 900 ml. of acetic acid and 36 ml. of water. 53.3 g. (0.32 mole) of silver acetate is added followed by 40.6 g. (0.16 g-atom) of iodine. The slurry is heated with good stirring at 85° ± 10° for 3 hr. under nitrogen, cooled and filtered. The filtrate is evaporated in vacuo and the residue dissolved in 250 ml. of methanol and cooled to 0°. A solution of 40 g. of sodium hydroxide in 200 ml. of water is added under nitrogen and the mixture stirred overnight. The bulk of the methanol is removed in vacuo whereupon a solid forms. The solid is separated by filtration, dissolved in 150 ml. of water and acidified with 20 ml. of concentrated hydrochloric acid. Cooling gives a solid which is filtered and dried to give 16.5 g. 2,3-cis-5,6,7,8-tetrahydro-1,6,7-naphthalenetriol) m.p. 184.5°–187°. Three recrystallizations from absolute ethanol give the analytical sample, m.p. 188°–188.5°.

Anal. Calc'd for $C_{10}H_{12}O_3$: C, 66.65; H, 6.71. Found: C, 66.19; H, 6.68.

b. 2,3-cis-1,2,3,4-Tetrahydro-5-[2,3-(epoxy)-2,3-naphthalenediol -propoxy]-2,3,-naphthalenediol A solution of 1.20 g. (0.03 mole) of sodium methoxide and 5.4 g. (0.03 mole) of cis-5,6,7,8-tetrahydro-1,6,7-naphthalenetriol in 200 ml. of methanol is prepared under nitrogen. The residue obtained upon solvent removal is stirred overnight with 200 ml. of dimethylsulfoxide and 4.65 g. (0.05 mole) of epichlorohydrin under nitrogen. The bulk of the solvent is removed at 50° at 0.1 mm. and the residue dissolved in 500 ml. of water. Extraction with chloroform (10 × 200 ml.) gives 3.46 g. of solid which is recrystallized from 150 ml. of hexane-ethyl acetate to give 2.80 g. of epoxy diol of the above title, m.p. 108°–111.5°.

c. 2,3-cis-1,2,3,4-Tetrahydro-5-[2-hydroxy-3-(isopropylamino)-propoxy]-2,3-naphthalenediol A solution of 2.75 g. (0.011 mole) of 2,3-cis-1,2,3,4-tetrahydro-5-[2,3-(epoxy)-propoxy]-2,3-naphthalenediol in 20 ml. of isopropylamine is heated at 80° ± 5° in a Parr bomb (press. ≅ 40 lb/in$^2$) for 16 hr. The excess amine is removed in vacuo and the residue recrystallized twice from 350 ml. of benzene to give 2.32 g., m.p. 112°–120.5°.

Anal. Calc'd for $C_{16}H_{25}NO_4$: C, 65.06; H, 8.53; N, 4.74. Found: C, 65.27; H, 8.65; N, 4.61.

EXAMPLE 6

1,2,3,4-Tetrahydro-5-[2-hydroxy-3-(benzylisopropylamino)-propoxy]-2(and 3)-naphthol A solution of 3.26 g. (0.0093 mole) of 1-(5,8-dihydro-1-naphthyloxy)-3-(benzyl isopropylamino)-2-propanol (prepared as disclosed in application Ser. No. 768,176, issued Oct. 13, 1970 as U.S. Pat. No. 3,534,085) in 25 ml. of dry tetrahydrofuran is treated dropwise with a solution of 0.1 mole of borane in tetrahydrofuran. After stirring for 16 hours, the mixture is freed of solvent and the residue taken up in 25 ml. of 95% ethanol and treated with 0.8 (0.02 mole) of sodium hydroxide followed by dropwise addition of 2.5 ml of 30% hydrogen peroxide (0.02 mole). After a 2½ hour period at reflux the mixture is taken to near dryness in vacuo and the product extracted into ether. Chromatography on activity II neutral alumina affords the two isomeric alcohols of the above title.

EXAMPLE 7

1,2,3,4-Tetrahydro-5-[2-hydroxy-3-(isopropylamino)-propoxy]-3-naphthol

Following the procedure described in Example 3, but substituting 7-methoxy-1-tetralone for 6-methoxy-1-tetralone, the above titled compound is prepared.

EXAMPLE 8

1,2,3,4-Tetrahydro-5-[2-hydroxy-3-(isopropylamino)-propoxy]-2(and 3) naphthol a. 5,6,7,8-Tetrahydro-1,6 (and 7) naphthalenediol To a well stirred suspension of 5 g. of lithium aluminum hydride in 100 ml. of ether is added dropwise a solution of 8.0 g. (0.048 mole) of 5,6,7,8-tetrahydro-6,7-epoxy-1-naphthol in 100 ml. ether. After several hours under reflux, the mixture is treated with aqueous acid, and the products isolated from the organic solvents.

b. 1,2,3,4-Tetrahydro-5-[2,3-(epoxy)-propoxy]-2(and 3) naphthol

A solution of 3.28 g. (0.02 mole) of the mixture of diols in 100 ml. of methanol is cooled to 0° and 1.08 g. (0.02 mole) of sodium methoxide in methanol added. The solvent is removed in vacuo and the residue heated at 50° under 0.05 mm. for 1 hour, dissolved in 80 ml. of dimethylsulfoxide and stirred overnight under nitrogen with 3.68 g. (0.04 m.) of epichlorohydrin. After removal of solvent in vacuo, the residue is dissolved in 250 ml. of water and extracted three times with chloroform. After washing with 5% sodium hydroxide and saturated salt solution, solvent is removed to leave crude product recrystallized from benzene-petroleum ether.

c. 1,2,3,4-Tetrahydro-5-[2-hydroxy-3-(isopropylamino)-propoxy]-2 (and 3) naphthol A solution of 2.2 g. (0.01 mole) of 1,2,3,4-tetrahydro-5-[2,3-(epoxy)-propoxy]-2 (and 3) naphthol in 15 ml. of isopropylamine is heated at 80° ± 5° for 16–20 hours in a Parr bomb. The cooled solution is taken to dryness and the residue crystallized from benzene-petroleum ether to give the above titled mixture.

EXAMPLE 9

2-Acetoxy-1,2,3,4-tetrahydro-5-[(2-hydroxy-3-(isopropylamino)propoxy]-naphthalene a. 3-Isopropyl-5-(5,6,7,8-tetrahydro-6-hydroxy-1-naphthoxy)methyl oxazolidine hydrochloride A solution of 5.58 g. (0.02 mole) of 1,2,3,4-tetrahydro-5-[2-hydroxy-3-(isopropylamino)propoxy]-2-naphthol in 30 ml. of 99% ethanol is treated with 4 ml. of 33% formalin and heated under reflux for 12–16 hours. The solution is acidified with hydrochloric acid in ethanol and the oxazolidine hydrochloride precipitated by the addition of ether.

b. 2-Acetoxy-1,2,3,4-tetrahydro-5-[(2-hydroxy-3-(isopropylamino)propoxy]-naphthalene The oxazolidine hydrochloride is dissolved in dry pyridine and treated with 0.1 mole of acetic anhydride at room temperature. After several hours standing, the mixture is poured into water and made acid with dilute hydrochloric acid. After stirring for several hours, the mixture is basified with aqueous ammonia in the cold and the product isolated by extraction into chloroform, drying and solvent removal.

EXAMPLES 10 to 15

By substituting a 1-(2,3-epoxy-propoxy)-5,8-dihydro-naphthalene as shown in the left hand first column of Table I for the corresponding starting material in Example 1a and employing the procedure of Example 1a, a 2,3-epoxypropyl-6,7-epoxy-5,6,7,8-tetrahydro-1-naphthyl ether is formed. By reacting the naphthyl ether with an amine of the structure

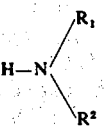

employing the procedure of Example 1b, and thereafter reacting the resulting product (as shown in the middle column of Table I) with LiAlH$_4$ employing the procedure of Example 2, the product shown in the right hand (third) column of Table I is produced.

TABLE I

| Example | $R^3$ | $R^4$ | $R^5$ | $R^6$ | $R^7$ | $R^8$ | $R^9$ | $R^{10}$ | $R^3$ to $R^{10}$ same as in Col. 1 | $R^1$ | $R^2$ | $R^1$ to $R^{10}$ same as in cols. 1 and 2 | Z | $Z^1$ |
|---|---|---|---|---|---|---|---|---|---|---|---|---|---|---|
| 10 | H | CH$_3$ | H | CH$_3$ | H | CH$_3$ | H | H | " | H | C$_4$H$_9$ | " | OH | H |
| 11 | C$_2$H$_5$ | C$_2$H$_5$ | C$_2$H$_5$ | H | H | H | NH$_2$ | H | " | —(CH$_2$)$_2$OH | H | " | H | OH |
| 12 | C$_6$H$_{13}$ | H | CH$_3$ | H | H | CH$_3$ | CH$_3$ | H | " | ⌬-CH$_2$ | CH$_3$ | " | OH | — |

Table I-continued

| | R¹² | R⁸ | R⁹ | R¹⁰ | R⁸–R¹⁰ as in Col. 1 | R⁸ to R¹⁰ as in Col. 1 | R³ | R⁴ | R⁵ | R⁶ | R⁷ | R¹ | R² |
|---|---|---|---|---|---|---|---|---|---|---|---|---|---|
| 13 | t-C₄H₉ | H | H | t-C₄H₉ | H | CH₃ | CH₃ | CH₃ | '' | H | —NH CH₃ | '' | — | OH |
| 14 | H | H | C₃H₇ | H | H | COOH | H | H | '' | —N‿NH | '' | OH | — |
| 15 | H | H | H | H | H | ◁ | H | H | '' | —N‿O | '' | — | OH |

EXAMPLES 16 – 21

Employing the procedure of Example 3 (a), but substituting a 6-alkoxy-1-tetralone as shown in the left hand (first) column of Table II for 6-methoxy-1-tetralone, a 6-alkoxy-1-naphthol is produced, which is converted as per Example 3 (b) to the corresponding 5-hydroxy-3,4-dihydro-2(1 H)-naphthalenenone shown in the middle column of Table II; employing the procedure of Example 3 (c) the naphthalenone is converted to the corresponding 5,6,7,8-tetrahydro-1,6-naphthalenediol which is reacted with an epoxide of the structure

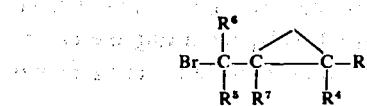

in accordance with the procedure of Example 3 d to form the corresponding 1,2,3,4-tetrahydro-5-[2,3-epoxy-propoxy]-2-naphthol which is reacted with an amine of the structure

in accordance with the procedure of Example 3 e to form the corresponding 1,2,3,4-tetrahydro-5-[2-hydroxy-3-(R¹, R²-substituted amino)propoxy]-2-naphthol (formula I) as shown in the right hand (third) column of Table II.

TABLE II

| Example | R¹² | R⁸ | R⁹ | R¹⁰ | R⁸–R¹⁰ as in Col. 1 | R⁸ to R¹⁰ as in Col. 1 | R³ | R⁴ | R⁵ | R⁶ | R⁷ | R¹ | R² |
|---|---|---|---|---|---|---|---|---|---|---|---|---|---|
| 16 | C₂H₅ | H | CH₃ | H | '' | '' | H | H | H | C₃H₁₁ | CH₃ | H | H |
| 17 | t-C₄H₉ | H | H | t-C₄H₉ | '' | '' | i-C₃H₇ | H | C₂H₅ | H | H | H | ⟨O⟩-NH |
| 18 | i-C₃H₇ | C₅H₁₁ | H | H | '' | '' | C₂H₅ | CH₃ | H | H | H | -N⟨⟩ |  |
| 19 | CH₃ | CH₃O | CH₃ | H | '' | '' | H | H | H | C₆H₁₃ | H | -N⟨⟩S |  |
| 20 | C₆H₁₃ | C₃H₇ | H | COOH | '' | '' | H | H | H | H | CH₃ | CH₃-CH⟨⟩ |  |
| 21 | C₅H₁₁ | H | H | NH₂ | '' | '' | H | CH₃ | H | CH₃ | H | CH₃ | CH₃ |

EXAMPLES 22 to 27

Following the procedure of Example 4(a) but substituting the substituted 5,8-dihydro-1-naphthol shown in the left hand most (first) column of Table III for 5,8-dihydro-1-naphthol, the 5,6,7,8-tetrahydro-6,7-epoxy-1-naphthol shown in the second column is formed. Following the procedure of Example 4(b), the 1-naphthol in the second column is converted to the 5,6,7,8-tetrahydro-1,6,7-naphthalenetriol set out in the third column of Table III. The naphthalenetriol is then reacted with sodium methoxide and an epoxide of the structure

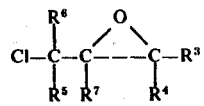

in accordance with the procedure of Example 4(c) to form a 2,3-trans-1,2,3,4-tetrahydro-5-[2,3-(epoxy)-propoxy]-2,3-naphthalenediol which is reacted with a $R^1$, $R^2$-substituted amine in accordance with the procedure of Example 1(d) to form the product shown in the right hand most (fourth) column of Table III.

TABLE III

| Ex. | $R^8$ | $R^9$ | $R^{10}$ | $R^8$ – $R^{10}$ same as in Col. 1 | $R^8$ – $R^{10}$ same as in Col. 1 | $R^1$ | $R^2$ | $R^3$ | $R^4$ | $R^5$ | $R^6$ |
|---|---|---|---|---|---|---|---|---|---|---|---|
| 22 | COOH | H | H | " | " | –N⟨⟩NH | | H | $CH_3$ | H | H |
| 23 | H | ◁ | H | " | " | –N⟨⟩ | | $C_2H_5$ | $CH_3$ | H | H |
| 24 | H | H | $NH_2$ | " | " | –N⟨⟩O | | H | H | $C_6H_{13}$ | $C_2H_5$ |
| 25 | $C_2H_5O$ | H | $CH_3$ | " | " | –N⟨⟩ | | H | $-C_3H_7$ | $CH_3$ | H |
| 26 | $CH_3$ | $CH_3$ | $CH_3$ | " | " | $CH_3$ | | $CH_3$ | H | H | $C_2H_5$ | H |
| 27 | ⟨C₆H₅⟩–$CH_2$– | H | H | " | " | H | | H | H | H | H | $CH_3$ |

EXAMPLES 28 to 33

Following the procedure of Example 5(a), but substituting

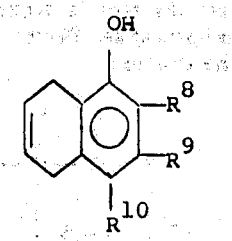

for the 5,8-dihydro-1-naphthol and reacting the above substituted naphthol with a carboxylic acid anhydride

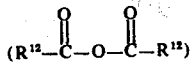

the compound shown in the left hand (first) column of Table IV is formed, which is reacted with silver acetate and iodine as in Example 5a to form a cis-5,6,7,8-tetrahydro-1,6,7-naphthalenetriol as shown in the middle column of Table IV. The triol is reacted with an epoxide of the structure

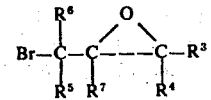

as per Example 5b to form a 2,3-cis-1,2,3,4-tetrahydro-5-[2,3-(epoxy)-propoxy]-2,3-naphthalenediol which is reacted with an $R^1$, $R^2$-substituted amine in accordance with Example 5(c) to form the product shown in the right hand column of Table IV.

TABLE IV

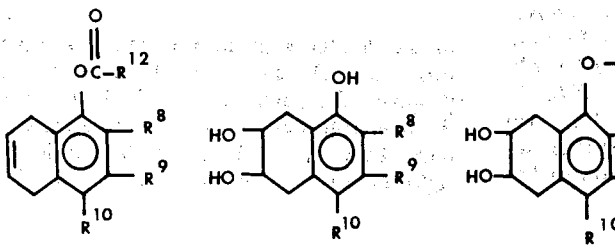

| Ex. | R¹² | R⁸ | R⁹ | R¹⁰ | R⁸-R¹⁰ same as in Col. 1 | R⁸-R¹⁰ same as in Col. 1 | R¹ | R² | R³ | R⁴ | R⁵ | R⁶ | R⁷ |
|---|---|---|---|---|---|---|---|---|---|---|---|---|---|
| 28 | $CH_3$ | COOH | H | H | " | " | $CH_3$ | $C_2H_5$ | H | H | $CH_3$ | H | $CH_3$ |
| 29 | $C_2H_5$ | $NH_2$ | H | H | " | " | $C_2H_5$ | $C_2H_5$ | H | $C_2H_5$ | $CH_3$ | $CH_3$ | $CH_3$ |
| 30 | $C_3H_7$ | H | $CH_3$ | $CH_3$ | " | " | –N⟨⟩NH | H | H | H | H | H | |
| 31 | C₆H₅– | H | $C_2H_5O$ | H | " | " | –N⟨⟩N–$(CH_3)_2OH$ | H | $C_6H_{13}$ | H | $CH_3$ | $CH_3$ | |
| 32 | C₆H₅–CH₂ | H | H | H | " | " | –N⟨⟩ | $CH_3$ | H | $CH_3$ | $CH_3$ | H | |
| 33 | $C_4H_9$ | $CH_3$ | $C_2H_5$ | $CH_3$ | " | " | H | i-$C_3H_7$ | H | $C_3H_7$ | H | $C_2H_5$ | $C_4H_9$ |

EXAMPLE 34

2,3-cis-1,2,3,4-Tetrahydro-5-[2-hydroxy-3-(tert-butylamino)propoxy]-2,3-naphthalenediol a. cis-5,6,7,8Tetrahydro-1,6,7-naphthalenetriol A solution of 29.2 g. (0.2 mole) of 5,8-dihydro-1-naphthol and 40 ml. of acetic anhydride in 100 ml. of pyridine is prepared. After 16 hr. the solvent is removed in vacuo and the residue dissolved in ether and washed with 200 ml. of 5% hydrochloric acid, water, 200 ml. of 10% sodium hydroxide, saturated salt solution and dried. Solvent removal gives 34.2 g. (90.5%) of crude acetate which is dissolved in 900 ml. of acetic acid and 36 ml. of water. 53.3 g. (0.32 mole) of silver acetate is added followed by 40.6 g. (0.16 g-atom) of iodine. The slurry is heated with good stirring at 85° ± 10° for 3 hr. under nitrogen, cooled and filtered. The filtrate is evaporated in vacuo and the residue dissolved in 250 ml. of methanol and cooled to 0°. A solution of 40 g. of sodium hydroxide in 200 ml. of water is added under nitrogen and the mixture stirred overnight. The bulk of the methanol is removed in vacuo whereupon a solid forms. The solid is separated by filtration, dissolved in 150 ml. of water and acidified with 20 ml. of concentrated hydrochloric acid. Cooling gives a solid which is filtered and dried to give 16.5 g. cis-5,6,7,8-tetrahydro-1,6,7-naphthalenetriol) m.p. 184.5°–187°. Three recrystallizations from absolute ethanol give the analytical sample, m.p. 188°–188.5°.

Anal. Calc'd for $C_{10}H_{12}O_3$: C, 66.65; H, 6.71. Found: C, 66.19; H, 6.68.

b. 2,3-cis-1,2,3,4-Tetrahydro-5-[2,3-(epoxy)-propoxy]-2,3-naphthalenediol

A solution of 1.20 g. (0.03 mole) of sodium methoxide and 5.4 g. (0.03 mole) of cis-5,6,7,8-tetrahydro-1,6,7-naphthalenetriol in 200 ml. of methanol is prepared under nitrogen. The residue obtained upon solvent removal is stirred overnight with 200 ml. of dimethylsulfoxide and 4.65 g. (0.05 mole) of epichlorohydrin under nitrogen. The bulk of the solvent is removed at 50° at 0.1 mm. and the residue dissolved in 100 ml. of water. Extraction with chloroform (10 × 200 ml.) gives a solid which is recrystallized from 150 ml. of hexane-ethyl acetate to give epoxy diol of the above title.

c. 2,3-cis-1,2,3,4-Tetrahydro-5-[2-hydroxy-3-(tert-butylamino)propoxy]-2,3-naphthalenediol A mixture of 3.0 g. of 2,3-cis-1,2,3,4-tetrahydro-5-[2,3-(epoxy)-propoxy]-2,3-naphthalenediol (m.p. 104°–107°, one spot on TLC–alumina, 5% methanol in chloroform, iodine visualization) and 22 ml of t-butyl amine is heated at 85°–95° for 15 hours in a Parr bomb and the excess amine removed in vacuo. The solid obtained by trituration of the residue with ether is filtered and recrystallized from benzene to give 3.4 g, m.p. 124°–136°.

Anal. Calcd for $C_{17}H_{27}NO_4$: C, 65.99; H, 8.80; N, 4.53. Found: C, 66.08; H, 8.88; N, 4.45.

What is claimed is:

1. A pharmaceutical composition useful for the treatment of coronary diseases in mammalian species in need thereof, comprising an effective amount of a compound having the structure

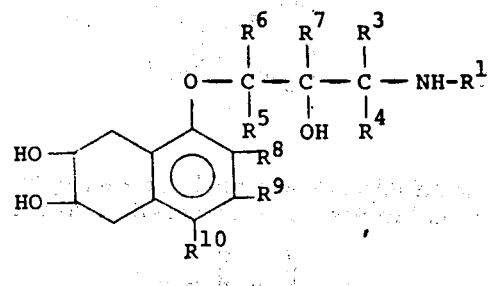

or a stereoisomer or salt thereof, wherein $R^1$ is lower alkyl; $R^3$, $R^4$, $R^5$, $R^6$ and $R^7$ are the same or different and are hydrogen or lower alkyl; and $R^8$, $R^9$ and $R^{10}$ are the same or different and are hydrogen, lower alkyl, lower alkoxy or cycloalkyl; and a pharmaceutically acceptable carrier therefor.

2. A pharmaceutical composition in accordance with claim 1 comprising an effective amount of a compound having the formula

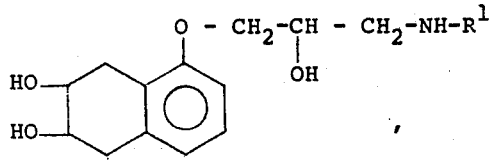

or a stereoisomer or salt thereof, and a pharmaceutically acceptable carrier therefor.

3. A pharmaceutical composition in accordance with claim 2 comprising an effective amount of a compound having the formula

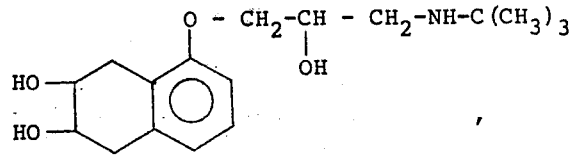

or a stereoisomer or salt thereof, and a pharmaceutically acceptable carrier therefor.

4. A pharmaceutical composition in accordance with claim 3 comprising an effective amount of 2,3-cis-1,2,3,4-tetrahydro-5-[2-hyroxy-3-(tert-butylamino)-propoxy]-2,3-naphthalenediol and a pharmaceutically acceptable carrier therefor.

* * * * *

UNITED STATES PATENT AND TRADEMARK OFFICE
CERTIFICATE OF CORRECTION

PATENT NO. : 3,982,021
DATED : September 21, 1976
INVENTOR(S) : Frederic P. Hauck et al.

It is certified that error appears in the above-identified patent and that said Letters Patent are hereby corrected as shown below:

Column 27, line 67, "$cm^{-2}$" should read -- $cm^{-1}$ --.

Column 31, line 13, "(epoxypropoxy]" should read -- (epoxy)propoxy] --.

Column 31, lines 56 and 57, the title of part b. should read: -- 2,3-cis-1,2,3,4-Tetrahydro-5-[2,3-(epoxy)-propoxy]-2,3-naphthalenediol --.

Column 36, example 13, "-NH " should read:

-- 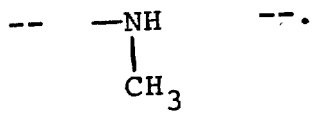 --.

Column 38, example 25, under $R_4$ should read:

-- $i-C_3H_7$ --.

Signed and Sealed this

Fourth Day of January 1977

[SEAL]

Attest:

RUTH C. MASON
*Attesting Officer*

C. MARSHALL DANN
*Commissioner of Patents and Trademarks*